United States Patent [19]

Archibald et al.

[11] Patent Number: 4,900,750
[45] Date of Patent: Feb. 13, 1990

[54] 1.4-DIHYDROPYRIDINES

[75] Inventors: John L. Archibald, Farnham Royal; Terence J. Ward; Albert Opalko, both of Maidenhead, all of England

[73] Assignee: John Wyeth & Brother, Limited, Maidenhead, United Kingdom

[21] Appl. No.: 81,526

[22] Filed: Aug. 3, 1987

Related U.S. Application Data

[63] Continuation of Ser. No. 930,973, Nov. 13, 1986, abandoned, which is a continuation of Ser. No. 760,708, Jul. 30, 1985, abandoned.

[30] Foreign Application Priority Data

Aug. 17, 1984 [GB] United Kingdom ................ 8421039

[51] Int. Cl.$^4$ ................ C07D 401/14; A61K 31/415; A61K 31/44
[52] U.S. Cl. .................................... 514/335; 514/332; 514/333; 514/334; 514/338; 514/341; 546/255; 546/256; 546/257; 546/258; 546/261; 546/271; 546/278
[58] Field of Search ............... 546/255, 256, 257, 258, 546/261, 271, 278; 514/332, 333, 334, 335, 338, 341

[56] References Cited

U.S. PATENT DOCUMENTS 4,492,703  1/1985  Goldmann et al. ................ 546/321

FOREIGN PATENT DOCUMENTS 0060674  9/1982  European Pat. Off. .
88274    9/1983  European Pat. Off. .
0089167  9/1983  European Pat. Off. .
100189   2/1984  European Pat. Off. .
0106462  4/1984  European Pat. Off. .
0125803  4/1984  European Pat. Off. .
1670825  3/1971  Fed. Rep. of Germany .
2844595  4/1980  Fed. Rep. of Germany .
1552911  9/1979  United Kingdom .
1560280  2/1980  United Kingdom .

OTHER PUBLICATIONS

Meark index, 9th Edition pp. 1047-1048.

Aritomi et al., Chem. Pharm. Bull., 28, 3163-3171(1980): Chem. Abst. 94:156707a.

Primary Examiner—Jane T. Fan
Attorney, Agent, or Firm—Arthur G. Seifert

[57] ABSTRACT

This invention concerns compounds of formula

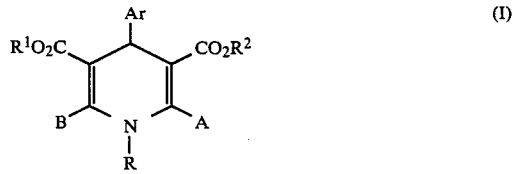

or salts thereof, wherein:

Ar is an optionally substituted aryl radical;

R represents hydrogen or an optionally substituted alkyl, aralkyl, or aryl group;

$R^1$ and $R^2$ are the same or different and are selected from hydrogen and saturated or unsaturated, cyclic or acyclic aliphatic hydrocarbon residues optionally substituted by one or more groups selected from halogen, OH, carboxy, CN, alkoxy, alkylthio, aryloxy, alkoxycarbonyl, amino, substituted amino, and optionally substituted aryl;

A and B independently represent a group of formula —$XR^3$ wherein

X is a group of formula —$(CHR^6)_pY(CHR^7)_q$— wherein

Y represents —O—, —S—, —$NR^8$— or a direct bond; p and q each represent 0, 1 or 2 providing that p and q do not both represent O when Y is a direct bond; and $R^6$, $R^7$ and $R^8$ are independently hydrogen or alkyl; and $R^3$ is an optionally substituted nitrogen ring heteroaryl radical optionally containing other ring heteroatoms selected from oxygen, nitrogen and sulphur; which compounds possess pharmaceutical activity particularly inhibition of blood platelet aggregation and thromboxane synthetase.

23 Claims, No Drawings

1,4-DIHYDROPYRIDINES

This application is a continuation of application Ser. No. 930,973, filed Nov. 13, 1986 now abandoned, which is a continuation of application Ser. No. 760,708, filed July 30, 1985, now abandoned.

This invention relates to heterocyclic compounds possessing pharmaceutical activity more particularly to 1,4-dihydropyridines, processes for preparing them and pharmaceutical compositions containing them.

In one aspect this invention provides compounds of formula

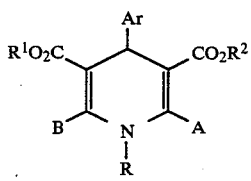

or salts thereof, wherein:
Ar is an optically substituted aryl radical;
R represents hydrogen or an optionally substituted alkyl, aralkyl, or aryl group;
$R^1$ and $R^2$ are the same or different and are selected from hydrogen and saturated or unsaturated, cyclic or acyclic aliphatic hydrocarbon residues optionally substituted by one or more groups selected from halogen, OH, carboxy, CN, alkoxy, alkylthio, aryloxy, alkoxycarbonyl, amino, substituted amino, and optionally substituted aryl;
A and B independently represent a group of formula —$XR^3$ wherein
X is a group of formula —$(CHR^6)_pY(CHR^7)_q$— wherein Y represents —O—, —S—, —$NR^8$— or a direct bond; p and q each represent 0, 1 or 2 providing that p and q do not both represent 0 when Y is a direct bond; and $R^6$, $R^7$ and $R^8$ are independently hydrogen or alkyl; and $R^3$ is an optionally substituted nitrogen ring heteroaryl radical optionally containing other ring heteroatoms selected from oxygen, nitrogen and sulphur.

The term lower as used herein to qualify a group means the group contains 1 to 6 carbon atoms.

By the term aryl when used as a group or part of a group (e.g. aryloxy, arylalkyl) is meant any monovalent carbocyclic or heterocyclic radical processing aromatic character and includes such groups having 5 to 10 ring carbon atoms such as phenyl, naphthyl, pyridyl (e.g. 2-, 3- or 4- pyridyl), thienyl (e.g. 2-thienyl), furyl (e.g. 2-furyl), quinolyl (e.g. 2-, 3- or 4-quinolyl), isoquinolyl, (e.g. 2-, 3- or 4-isoquinolyl). Preferred heteroatoms are nitrogen, oxygen and sulphur. Examples of heterocyclic aromatic rings containing two heteroatoms are imidazolyl e.g. 1-imidazolyl, and thiazolyl, e.g. 5-thiazolyl.

The term alkyl when used to signify a group or part of a group such as arylalkyl or alkyloxy means any straight or branched saturated aliphatic hydrocarbon especially those having 1 to 6 carbon atoms, e.g. 1-4 carbon atoms, or cyclic saturated aliphatic hydrocarbons especially those of 5 to 7 carbon atoms. Examples are methyl, ethyl, n-propyl, isopropyl, n-butyl, n-hexyl and cyclohexyl.

By the term 'optionally substituted' is meant optional substitution on carbon atoms by one or more substituents, e.g. substituents commonly used in pharmaceutical chemistry, e.g. halogen (e.g. Cl, Br, F), alkyl, alkyloxy, haloalkyl (e.g. $CF_3$) haloalkoxy (e.g. $CF_3CH_2O$—, $CHF_2O$—), $NO_2$, $NH_2$, CN, alkylamino, dialkylamino, carboxy, alkyloxycarbonyl, acyl, acylamino.

Examples of the group R are groups as described above in connection with alkyl, aryl and arylalkyl and include hydrogen, methyl, ethyl, n-propyl, isopropyl and benzyl. Preferably R is hydrogen.

The groups $R^1$ and $R^2$ can be independently hydrogen or saturated or unsaturated acyclic hydrocarbon chains of 1 to 6 carbon atoms, e.g. lower alkyl or alkenyl optionally substituted by aryl of 5 to 10 carbon atoms, lower alkoxy, amino, diloweralkylamino, carboxyl or lower alkoxycarbonyl.

Examples of $R^1$ and/or $R^2$ are methyl, ethyl, n-propyl, isopropyl, butyl, methoxymethyl, methoxyethyl, ethoxymethyl, ethoxyethyl, methoxypropyl, aminomethyl, 2-aminoethyl, 3-aminopropyl, dimethylaminoethyl, 2-carboxyethyl, ethoxycarbonylmethyl. When $R^1$ or $R^2$ is alkyl substituted by optionally substituted aryl (including heteroaryl) examples are pyridylmethyl or -ethyl (e.g. 3-pyridylmethyl)imidazolylmethyl or -ethyl.

Preferred values for $R^1$ and/or $R^2$ are methyl and ethyl.

Examples of $R^3$ and are imidazolyl (e.g. 1 or 3-imidazolyl), pyridyl (e.g. 2 or 3-pyridyl), thiazolyl (e.g. 5-thiazolyl), pyrrolyl (e.g. 1-pyrrolyl) or bicyclic rings such as quinolyl (e.g. 2- or 4-quinolyl), isoquinolyl (e.g. 1- or 4-isoquinolyl), imidazopyridyl (e.g. 5-imidazo [1,5-a]-pyridyl). Preferred values are 1-imidazolyl, 3-pyridyl and 5-imidazo[1,5-a]pyridyl.

Examples of X are —NH—; —O—; —S—; —$CH_2$—; —$CH(CH_3)$—; —$CH_2O$—; —$OCH_2$—; —$(CH_2)_2$— —$CH_2CH(CH_3)$— or groups of formula —$CH_2$—Z—$CH_2$—, —$CH_2$—Z—$(CH_2)_2$—, —$CH_2)_2$—Z—$CH_2$— where Z is O, S, NH or a direct bond.

Preferred examples of X are —$CH_2O$—, —$CH_2OCH_2$—, —$CH_2O(CH_2)_2$—, —$CH_2$— or —$CH_2CH_2$—.

Examples of Ar are groups mentioned above for the definitions of aryl and included in the preferred values are 2- and/or 3- substituted phenyl groups, e.g. 2- and/or 3-nitrophenyl; 2,3-dichlorophenyl; 2-trifluoromethylphenyl; pentafluorophenyl; naphthyl (e.g. 1-naphthyl), pyridyl (e.g. 2-pyridyl), halopyridyl (e.g. 2-chloropyrid-3-yl), benzimidazolyl (e.g. 4- or 7-benzimidazolyl).

Particularly preferred compounds provided by this invention have formula Ia:

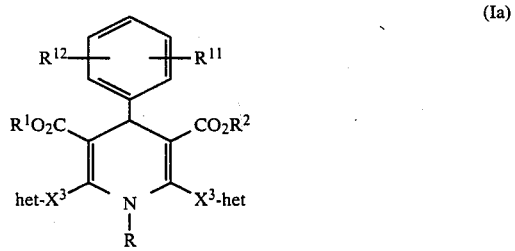

wherein R,$R^1$ and $R^2$ have the meanings given above het represents a pyridyl or imidazolyl group, $X^3$ is —$CH_2$—, —$CH_2OCH_2$—, —$CH_2O(CH_2)_2$—, —$CH_2CH_2$—, —$(CH_2)_2OCH_2$— or —$(CH_2)_2O(CH_2)_2$—; $R^{11}$ and $R^{12}$ are each selected from hydrogen, nitro, halo or trifluoromethyl, or a salt thereof.

In formula Ia preferably R is hydrogen.

Examples of $R^1$ are H, Me or Et. Examples of $R^2$ are Me and Et. When $R^{11}$ is hydrogen examples of $R^{12}$ are 2- or 3-nitro, 2-trifluoromethyl. Examples of $R^{11}$ and $R^{12}$ when substituents are 2,3-dihalo, (e.g. 2,3-dichloro), 3-halo-2-nitro and 2-halo-3-nitro. Preferably both het groups are the same e.g. 3-pyridyl or 1-imidazolyl. Preferably both $X^3$ groups are the same.

The compounds of formula I possess pharmaceutical activity in particular they inhibit thromboxane synthetase and inhibit blood platelet aggregation.

Since platelet aggregation is the initial step in thrombus formation it is considered that compounds which prevent aggregation or reduce platelet adhesiveness may inhibit the initiation of the atherosclerotic process. The effect of drugs on aggregation is measured in platelet-rich plasma containing a small amount of arachidonic acid which markedly increases aggregation in vitro and may be a physiological agent for doing so in vivo. The actual test procedure used is described below.

New Zealand white rabbits (2.5-3 kg) are anaesthetised with an injection, via the marginal ear vein, of sodium pentobarbitone 30-40 mg/kg. The carotid artery is cannulated and blood (100-150 ml) is withdrawn into 50 ml syringes containing 3.8% sodium citrate (Ratio blood: citrate=9:1).

Blood is centrifuged at 200 g (1500 r.p.m.) for 10 minutes at 5° C. and the platelet rich plasma (PRP) removed. The platelets are then kept at room temperature in a screw topped plastic centrifuge tube for the duration of the experiment.

A twin channel platelet aggregometer -(HU aggregometer, A. Browne Ltd, Leicester, UK) is used. 1.0 ml aliquots of PRP are prewarmed for 5-10 minutes and stirred continuously at 1100 rpm. Aggregation is induced by addition of 250 $\mu$M arachidonic acid, (8 $\mu$l volume) to the PRP samples. The aggregometer output is set at maximum and the chart recorder sensitivity is altered to give a full scale deflection to this arachidonic acid response.

Control responses are recorded as the maximum deflection obtained after addition of 250 $\mu$M arachidonic acid.

PRP samples are preincubated for 1 minute with the test compounds followed by arachidonic acid addition. The maximum deflection after the addition of arachidonic acid is then recorded. All drugs are screened initially at $10^{-4}$M (final concentration), i.e. 10 $\mu$l of a $1\times10^{-2}$M stock solution of the drug dissolved in distilled water is added to the PRP.

Dazoxiben, a thromboxane synthetase inhibitor (Randall, M. J. et al, Research 23 145-162, 1981) is used as a positive control and all test components are compared with Dazoxiben. The activity of the test compound is expressed as the ratio IC$_{50}$ Dazoxiben/IC$_{50}$ Test where IC$_{50}$ is the dose required to inhibit the A.A. induced aggregation by 50%. The greater the ratio the more potent the compound relative to Dazoxiben.

| COMPOUND | Inhibition of blood platelet aggregation potency ratio (dazoxiben = 1) |
|---|---|
| 1,4-Dihydro-2,6-di [(3-pyridyl-methoxy)methyl]-4-(3-nitrophenyl)-pyridine-3,5-dicarboxylic acid diethyl ester | 0.5 |
| 1,4-Dihydro-2,6-di [(3-pyridyloxy)-methyl]-4-(3-nitrophenyl)pyridine-3,5-dicarboxylic acid diethyl ester | 0.9 |
| 1,4-Dihydro-2,6-di [2-(imidazol-1-yl)-ethyl]-4-(3-nitrophenyl)pyridine-3,5-dicarboxylic acid diethylester | 0.7 |
| 1,4-Dihydro-2,6-di[(3-pyridylmethoxy)-methyl]-4-(2-nitrophenyl)pyridine-3,5-dicarboxylic acid diethyl ester | 2.2 |

Compounds possessing thromboxane synthetase inhibitory activity are useful in the treatment or prevention of diseases responsive to the inhibition of thromboxane synthetase especially cardiovascular disorders such as thrombosis, atherosclerosis, cerebral ischaemic attacks; and angina pectoris; peripheral vascular diseases and migraine.

The compounds of formula I were tested for their ability to inhibit thromboxane production by the following standard test:

(a) Generation of thromboxane

Blood (approx. 75 ml) is obtained from an anaesthetised rabbit and centrifuged at 200 g for 10 minutes to obtain platelet rich plasma (PRP). An aliquot of PRP is incubated for 10 minutes at 37° C. in the presence of vehicle or drug. Platelet aggregation is induced by the addition of adenosine diphosphate and adrenalin. The tubes are incubated for 3 minutes, centrifuged at 10,000 g for 3 minutes and a 50 ml aliquot of the supernatant taken for radio-immunoassay of thromboxane $B_2$ (TxB$_2$).

(b) Radio-immunoassay of TxB$_2$

The total incubation volume is 150 $\mu$l containing 50 $\mu$l of $^3$H-TxB$_2$ (0.005 $\mu$Ci), 50 ml of sample or authentic TxB$_2$ ranging from 5 to 300 pg per tube as standards and 50 $\mu$l of rabbit anti-sera to TxB$_2$ (in a concentration which will bind 50% of H-TxB$_2$). After incubation for 1 hour at room temperature the tubes are further incubated for 16-20 hours at 4° C. 1 ml of dextran-coated charcoal is then added to the tubes which are further incubated on ice for 10 minutes. Following the incubation the samples are centrifuged at 10,000 g for 10 minutes and 500 ml of the supernatant added to 5 ml of scintillation cocktail. Measurement of the radioactivity in the supernatant quantifies the amount of [$^3$H]-TxB$_2$ bound by the antibody. The concentration of unlabelled TxB$_2$ in the sample is then determined from a linear standard curve.

In the above mentioned test the compound 1,4-dihydro-2,6-di[2-(imidazol-1-yl)ethyl]-4-(3-nitrophenyl)-pyridine-3,5-dicarboxylic acid diethylester, had an IC$_{50}$ value of 5.3 $\mu$M. An IC$_{50}$ value represents the concentration of drug which achieves 50% inhibition of TxB$_2$.

Some compounds of formula I have also been found to possess Phospholipase A$_2$ (PLA$_2$) inhibitory activity and hence are also indicated for use as antiinflammatory and antiallergic agents. Of particular interest for this activity are compounds of formula I wherein Ar represents an aryl radical having a 2-nitro substituent. For example the compound of Example 2 produced a 72% inhibition of PLA$_2$ activity at a concentration of 100 $\mu$M. PLA$_2$ activity was assayed by a procedure based on Franson, R. C., Chapter 12. Intracellular Metabolism of Ingested Phospholipids. Liposomes: from Physical structure to Therapeutic Applications. North-Holland Biomedical Press, 1981, pp 349–380 and involving measuring the hydrolysis of E.coli membrane phospholipids and the release of free [1-$^{14}$C]oleic acid from the C-2 position of phospholipids by human platelet PLA$_2$.

Compounds of formula I have also shown antihypertensive activity when tested on warm blooded animals and hence are indicated for the treatment of high blood pressure. This latter activity in combination with their blood platelet and thromboxane synthetase inhibitory properties makes these compounds potentially very useful for the treatment of cardiovascular disorders, especially thrombosis.

Compounds of formula I were tested for antihypertensive activity by the following standard procedure:

The blood pressure of male or female spontaneously hypertensive rats are measured in a 37° C. constant temperature housing by means of a tail cuff. Rats with systolic pressures below 155 mmHg are discarded. Groups of rats are dosed orally with the test substance in a suitable vehicle or with vehicle alone. Systolic pressures are recorded before dosing and at selected time points afterwards. Heart rates are derived from caudal artery pulses. Results are analysed statistically by means of 2 way analysis of variance (within group).

In this procedure the compound of Example 2 at a dose level of 0.15 mmol/kg produced a 23% lowering of blood pressure, 2 hours after dosing.

This invention also provides processes for preparing the compounds of formula I. A first general process for preparing compounds of formula I as hereinbefore defined with the proviso that (a) when Y is —O—, —S— or —NR$^8$— then p is 1 or 2 comprises reacting corresponding compounds of formula

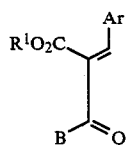

II

R—NH$_2$      III

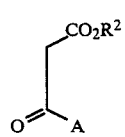

IV wherein Ar, A, B, R, R$^1$ and R$^2$ are as defined above.

In such a process, when B is a different group from A, in addition to the expected product having the formula

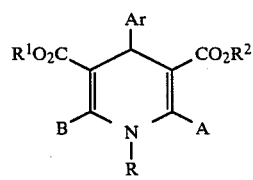

I it is also possible to obtain 'bis' compounds having the formula

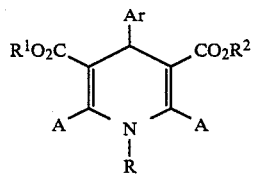

Ia

Accordingly compounds of formula I wherein B is A and proviso (a) applies may be prepared by compounds of formula

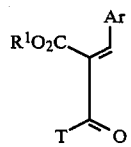

IIa with compounds of formulae III and IV

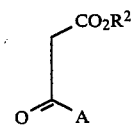

IV wherein Ar, R$^1$, R$^2$ and A are as defined above and T is an optionally substituted alkyl group.

The process is conveniently carried out by heating, e.g. at reflux, in an inert solvent preferably polar such as ethanol, toluene, dimethylformamide, isopropanol, acetonitrile.

A second general process for preparing compounds of formula I as hereinbefore defined and subject to proviso (a) as in the first process mentioned above, comprises reacting a corresponding compound of formula II as shown above with a corresponding compound of formula

(V)

wherein A, B, Ar, R, R$^1$ and R$^2$ are as defined above. This process may conveniently be carried out by heating e.g. at reflux in an inert solvent (preferably polar) such as ethanol, acetonitrile, isopropranol, toluene or dimethylformamide.

In yet a further process compounds of formula I wherein proviso (a) above applies may be prepared by reacting a compound of formula ArCHO with corresponding compounds of formula VI and V shown below

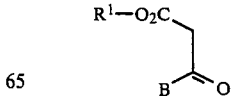

(VI)

and

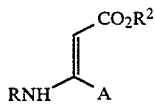

wherein Ar, R, $R^1$ and $R^2$ are as defined above. Such a process may be carried out by heating the reactants, e.g. at reflux, in an inert solvent (preferably polar) such as ethanol, acetonitrile, isopropranol, toluene or dimethylformamide.

A further process for preparing compounds of formula I as hereinbefore defined wherein B represents the same as the A group and proviso (a) above applies comprises reacting compounds of formula ArCHO $R\ NH_2$      (III), and

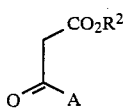

in which formulae Ar, R, $R^2$ and A are as defined immediately above. This process may be carried out by heating, e.g. at reflux in a suitable inert solvent, e.g. ethanol.

Compounds of formula I may be prepared by reacting corresponding compounds of formula

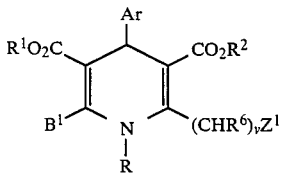

and $Z^2(CHR^7)_wR^3$      (VIII)

in which formulae Ar, R, $R^1$, $R^2$, $R^3$, $R^6$ and $R^7$ are as defined above, one of $Z^1$ and $Z^2$ is halogen or a sulphonyloxy group; the other of $Z^1$ and $Z^2$ is —YH or $Y^-$ as appropriate (wherein Y is as defined above) and v and w are each 0, 1 or 2 providing that (i) when v and w=0 then one of $Z^1$ and $Z^2$ is O, S or $NR^8$ and (ii) when v is 2 and $Z^2$ is YH or $Y^-$ then $Z^1$ can also represent dialkylamino, e.g. —$NMe_2$ or a quaternary ammonium group, e.g. —$NMe_3^+\ I^-$; and $B^1$ is B as defined above or $B^1$ is $Z^1(CHR^6)_v$— wherein $Z^1$, $R^6$ and v are as defined above.

The reaction may be carried out in an inert solvent in the presence of base, e.g. $K_2CO_3$ or a tertiary amine e.g. triethylamine. Anions of the requisite starting materials may be generated by the usual methods known in the art and reacted. Examples of sulphonyloxy are alkyl- or aralkyl- or aryl-sulphonyloxy, e.g. tosyloxy or mesyloxy.

The starting materials of formula VII wherein $Z^1$ is halogen, sulphonyloxy as defined above may be prepared by known methods, e.g. from corresponding compounds of formula

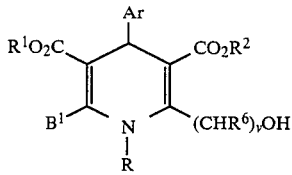

by methods known for the conversion of OH to halogen or sulphonyloxy. Compounds of formula VIII wherein v=0 may be prepared by reacting a compound of formula X

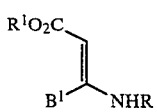

wherein R, $R^1$ and $B^1$ are as hereinbefore defined with compounds of formulae

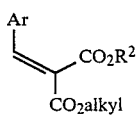

in which formula Ar and $R^2$ are as defined above.

Compounds of formula IX wherein v is 1 or 2 may be prepared by reacting a compound of formula

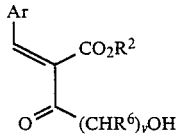

wherein v is 1 or 2 and Ar and $R^2$ are as defined above with a compound of formula (X) as hereinbefore defined.

Compounds of formula VII wherein v is 2 and $Z^1$ is —$N(alkyl)_2$ or a quaternary ammonium group may be prepared by performing a Mannich reaction on a compound of formula

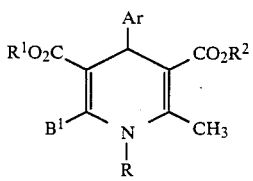

using formaldehyde and secondary amine and if required reacting the product with an alkyl halide. Compounds of formula VII wherein $Z^1$ is $Y^-$ may be prepared by known methods. For example, when $Z^1$ is —OH, —$NHR^8$ or —SH anions may be formed in the presence of a strong base, e.g. an alkali metal hydride such as NaH and BuLi. When Y is a direct bond carbanions may be prepared from the corresponding halo compound using for example, lithium diisopropylamine or BuLi.

In any of the aforementioned reactions reactive substituent groups may be protected if susceptible to the reaction conditions and deprotected afterwards.

Compounds of formula I wherein R is other than hydrogen may be prepared by alkylating a compound of formula I wherein R is H in the presence of a strong base, e.g. an alkali metal hydride, with a compound of formula R-halogen where R is as defined above other than hydrogen.

Compounds of formula I having ester functional groups, e.g. cyanoethyl- or t-butyl-ester, may be hydrolysed, selectively if appropriate, to give compounds of formula I having carboxyl groups. Alternatively carboxyl groups can be esterified.

The compounds of formula I may possess one or more asymmetric centres and hence optical isomers and mixtures thereof are possible. All such isomers and mixtures thereof are included within the scope of this invention. Where any reaction process produces mixtures of such isomers standard resolution techniques may be applied to a separate a specific isomer.

In any of the aforementioned reactions compounds of formula I may be isolated in free base form or as acid addition salts as desired. Examples of such salts include salts with pharmaceutically acceptable acids such as hydrochloric, hydrobromic, hydroiodic, sulphuric, phosphoric, nitric, acetic, citric, tartaric, fumaric, succinic, malonic, formic, maleic acid or organosulphonic acids such as methane sulphonic or p-tolyl sulphonic acids.

When acidic substituents are present it is also possible to form salts with bases e.g. alkali metal (such as sodium) or ammonium salts. Such salts of the compounds of formula I are included within the scope of this invention.

When basic substituents are present then quaternary ammonium salts may be formed by quaternizing with an alkylating agent such as alkyl-, aralkyl-halides.

Starting materials for the processes described herein are known compounds or can be prepared by analogous methods for known compounds.

This invention also provides pharmaceutical compositions comprising a compound of formula I or a pharmaceutically acceptable salt thereof.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavoring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10% to 75% of the glycol by weight is generally suitable. Other compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form.

The following Examples illustrate the preparation of compounds of the invention:

EXAMPLE 1

1,4-Dihydro-2,6-di[(3-pyridylmethoxy)methyl]-4-(3-nitrophenyl)pyridine-3,5-dicarboxylic acid diethyl ester Ethyl 3-oxo-4-(3-pyridylmethoxy)butanoic acid (2.4 g, 0.01 mol), m-nitrobenzaldehyde (0.8 g, 0.053 mol) and 0.880 ammonia (0.5 ml) in ethanol (50 ml) was refluxed for 30 hours. The solvent was removed under reduced pressure and the residue treated with 2N hydrochloric acid and diethyl ether. The aqueous extract was basified with ammonia, then extracted with chloroform. The extract was washed well with water, dried (MgSO$_4$) and evaporated to give a solid. This was dissolved in acetone and acidified with ethanolic HCl to give crystals of the title compound (2.1 g) mp 169°–171° C.

Analysis: $C_{31}H_{32}N_4O_8 \cdot 2HCl \cdot H_2O$ requires C, 54.79; H, 5.34; N, 8.24% Found: C, 54.56; H, 5.48; N, 7.89%.

EXAMPLE 2

1,4-Dihydro-2,6-di[(3-pyridylmethoxy)methyl]-4-(2-nitrophenyl)pyridine-3,5-dicarboxylic acid diethyl ester Ethyl 3-oxo-4-(3-pyridylmethoxy) butanoic acid (2.4 g, 0.01 mol), 2-nitrobenzaldehyde (0.8 g, 0.053 mol) and 0.880 ammonia (0.5 ml) in ethanol (50 ml) were refluxed for 48 hours. The solvent was removed under reduced pressure and the residue treated with 2N hydrochloric acid and diethyl ether, then separated. The aqueous phase was basified with 0.88 ammonia then extracted with chloroform (×3). The combined chloroform extracts were washed with water, dried (MgSO$_4$) and evaporated to give a residue which was dissolved in acetone and acidified with ethanolic HCl. The dihydrochloride salt of the title compound crystallised and was collected by filtration and dried, m.p. 142°–145° C.

Analysis: $C_{31}H_{32}N_4O_8 \cdot 2HCl$ requires C, 56.28; H, 5.18; N, 8.47%. Found: C, 56.25; H, 5.36; N, 8.25%.

EXAMPLE 3

1,4-Dihydro-2,6-di[(3-pyridyloxy)-methyl]-4-(3-nitrophenyl)pyridine-3,5-dicarboxylic acid diethyl ester Ethyl 3-nitrobenzylideneacetoacetate (6.47 g. 0.026 mol), ethyl 3-oxo-4-(3-pyridyloxy)butanoate (5.8 g, 0.026 mol) and 0.88 ammonia (2.5 ml) in ethanol were refluxed for 7 hours. The solvent was removed under reduced pressure and the residue partitioned between 2N hydrochloric acid and diethyl ether. The aqueous acid was extracted with chloroform and this was washed with dilute ammonia solution, dried (MgSO$_4$) and evaporated. The residue was purified by chromatography on silica with first chloroform then ethyl acetate as eluent to obtain the title compound. This was dissolved in ethanol and acidified with ethanolic HCl to give the dihydrochloride salt of the title compound (0.95 g) m.p. 206–208° C.

Analysis: $C_{29}H_{28}N_4O_8.2HCl$ requires C, 54.98; H, 4.77; N, 8.84%. Found: C, 54.92; H, 5.26; N, 9.25%.

EXAMPLE 4

1,4-Dihydro-2,6-di[2-(imidazol-1-yl)ethyl]-4-(3-nitrophenyl)pyridine-3,5-dicarboxylic acid diethylester A mixture of 1,4-dihydro-2,6-di[3-(2-dimethylamino)ethyl]-4-(3-nitrophenyl)pyridine (2.52 g, 5 mmol) and imidazole (5.43 g, 80 mmol) was refluxed vigorously in chlorobenzene (40 ml) for 48 hours. More imidazole (1.36 g, 20 mmol) and chlorobenzene (10 ml) were added and refluxing was continued for a further 24 hours. After cooling, the chlorobenzene phase was washed three times with water, dried (MgSO$_4$) and evaporated. The residue was treated with acetone (30 ml) to give a solid product. This was suspended in boiling ethyl acetate (20 ml) and excess ethanolic HCl was added. The mixture was stirred in the dark for 10 minutes while cooling slowly, then the solid collected, washed with ethyl acetate and dried to give the title compound as the dihydrochloride, ¾ hydrate salt, mp. 210°–211° C.

Analysis: $C_{27}H_{30}N_6O_6.2HCl.\frac{3}{4}H_2O$ requires: C, 52.22; H, 5.44; N, 13.53%. Found: C, 52.30; H, 5.37; N, 13.62.

EXAMPLE 5

1,4-Dihydro-2,6-di[(3-pyridylethoxy)methyl]-4-(3-nitrophenyl)pyridine-3,5-dicarboxylic acid diethyl ester A mixture of ethyl 3-nitrobenzylideneacetoacetate (3.0 g), ethyl 3-oxo-4-[2-(pyrid-3-yl)ethyloxy]butanoate (3.0 g) and conc. ammonia (2 ml) in ethanol (50 ml) was refluxed for 6 hours. The solvent was removed under reduced pressure and the residue treated with ether and 2N hydrochloric acid, then separated. The aqueous acid phase was extracted with chloroform and the combined chloroform extracts washed with dilute ammonia solution, dried (NaSO$_4$) and evaporated.

The residue was purified by chromatography on silica firstly using ethyl acetate as eluent.

The eluent was changed to ethyl acetate and ethanol (4:1 v,v) to give the title compound (0.85 g). This was dissolved in ethanol, acidified with ethanolic HCl to give on crystallisation the title compound as the dihydrochloride ¾ hydrate, m.p. 132°–134° C.

Analysis: $C_{33}H_{36}N_4O_8.2HCl.\frac{3}{4}H_2O$ requires: C, 56.37; H, 5.66; N, 7.97%. Found: C, 56.11; H, 5.47; N, 8.40%.

We claim:
1. A compound of the formula

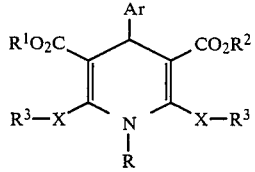

or a pharmaceutically acceptable salt thereof, wherein
Ar is 2- or 3-nitrophenyl, 2,3-dinitrophenyl, 2-3,dichlorophenyl, 3-chloro-2-nitrophenyl, 2-chloro-3-nitrophenyl, 2-trifluoromethylphenyl, pentafluorophenyl, naphthyl, pyridyl, mono-chloropyridyl, or 4- or 7-benzimidazolyl;
R is hydrogen, methyl, ethyl, n-propyl, isopropyl, benzyl, carbethoxymethyl or carbmethoxymethyl;
$R^1$ and $R^2$ are independently, selected from hydrogen, methyl, ethyl, n-propyl, isopropyl, butyl, methoxymethyl, ethoxymethyl, methoxypropyl, aminomethyl, 2-aminoethyl, 3-aminopropyl, dimethylaminoethyl, 2-carboxyethyl, methoxycarbonylmethyl, ethoxycarbonylmethyl, pyridylmethyl, pyridylethyl, imidazolylmethyl or imidazolethyl;
X is —CH$_2$O—, —CH$_2$OCH$_2$—, —CH$_2$O(CH$_2$)$_2$—, —CH$_2$— or —CH$_2$CH$_2$—; and
$R^3$ is 2-, or 3-pyridyl or 1- or 3-imidazolyl.

2. A compound of claim 1 in which Ar is 2- or 3-nitrophenyl, 2,3-dichlorophenyl, 2-trifluoromethylphenyl, pentafluorophenyl, 1-naphthyl, 2-pyridyl or 2-chloropyrid-3-yl.

3. A compound of claim 1 in which Ar is 2- or 3-nitrophenyl, 2-trifluoromethylphenyl, 2,3-dichlorophenyl, 3-chloro-2-nitrophenyl or 2-chloro-3-nitrophenyl.

4. A compound of claim 1 in which R is hydrogen.

5. A compound of claim 1 in which $R^1$ and $R^2$ are, independently, selected from methyl, ethyl, n-propyl, isopropyl, butyl, methoxymethyl, methoxyethyl, ethoxymethyl, ethoxyethyl, methoxypropyl, aminomethyl, 2-aminoethyl, 3-aminopropyl, dimethylaminoethyl, 2-carboxyethyl, ethoxycarbonylmethyl.

6. A compound of claim 1 in which $R^1$ is hydrogen, methyl or ethyl and $R^2$ is methyl or ethyl.

7. A compound of claim 1 in which $R^3$ is 3-pyridyl or 1-imidazolyl.

8. A compound of the formula

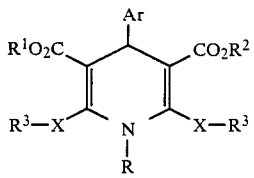

or pharmaceutically acceptable salts thereof, wherein
Ar is 2- or 3-nitrophenyl, 2,3-dichlorophenyl, 2-trifluoromethylphenyl, pentafluorophenyl, 1-naphthyl, 2-pyridyl or 2-chloropyrid-3-yl;
$R^1$ and $R^2$ are, independently, selected from methyl, ethyl, n-propyl, isopropyl, butyl, methoxymethyl, methoxyethyl, ethoxymethyl, ethoxyethyl, methoxypropyl, aminomethyl, 2-aminoethyl, 3-aminopropyl, dimethylaminoethyl, 2-carboxyethyl, ethoxycarbonylmethyl.
X is —CH$_2$O—, —CH$_2$OCH$_2$—, —CH$_2$O(CH$_2$)$_2$—, —CH$_2$— or —CH$_2$CH$_2$—; and
$R^3$ is 3-pyridyl or 1-imidazolyl.

9. A compound of claim 8 in which Ar is 2- or 3-nitrophenyl, 2-trifluoromethylphenyl, 2,3-dichlorophenyl, 3-chloro-2-nitrophenyl or 2-chloro-3-nitrophenyl.

10. A compound of claim 8 in which $R^1$ is hydrogen, methyl or ethyl and $R^2$ is methyl or ethyl.

11. A compound as claimed in claim 8 which is 1,4-dihydro-2,6-di[(3-pyridylmethoxy)methyl]-4-(3-nitrophenyl)pyridine-3,5-dicarboxylic acid diethyl ester or a pharmaceutically acceptable salt thereof.

12. A compound as claimed in claim 8 which is 1,4-dihydro-2,6-di[(3-pyridylmethoxy)methyl]-4-(2-nitrophenyl)pyridine-3,5-dicarboxylic acid diethyl ester or a pharmaceutically acceptable salt thereof.

13. A compound as claimed in claim 8 which is 1,4-dihydro-2,6-di[(3-pyridyloxy)methyl]-4-(3-nitrophenyl)pyridine-3,5-dicarboxylic acid diethyl ester or a pharmaceutically acceptable salt thereof.

14. A compound as claimed in claim 8 which is 1,4-dihydro-2,6-di[2-(imidazol-1-yl)ethyl]-4-(3-nitrophenyl)pyridine-3,5-dicarboxylic acid diethyl ester or a pharmaceutically acceptable salt thereof.

15. A compound as claimed in claim 8 which is 1,4-dihydro-2,6-di[(3-pyridylethoxy)methyl]-4-(3-nitrophenyl)pyridine-3,5-dicarboxylic acid diethyl ester or a pharmaceutically acceptable salt thereof.

16. A pharmaceutical composition comprising an amount of a compound of claim 1, or a pharmaceutically acceptable salt thereof, effective to lower blood pressure and a pharmaceutically acceptable carrier.

17. A pharmaceutical composition comprising an amount of a compound of claim 1, or a pharmaceutically acceptable salt thereof, effective to alleviate cardiac conditions susceptible to treatment by vasodilation and a pharmaceutically acceptable carrier.

18. A method of inhibiting blood platelet aggregation in a mammal, including man, in need thereof, comprising administering to such mammal an amount effective to inhibit blood platelet aggregation of a compound of the formula

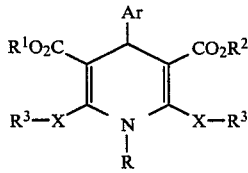

of a pharmaceutically acceptable salt thereof, wherein
Ar is 2- or 3-nitrophenyl, 2,3-dinitrophenyl, 2-3,dichlorophenyl, 3-chloro-2-nitrophenyl, 2-chloro-3-nitrophenyl, 2-trifluoromethylphenyl, pentafluorophenyl, naphthyl, pyridyl, mono-chloropyridyl, or 4- or 7-benzimidazolyl;
R is hydrogen, methyl, ethyl, n-propyl, isopropyl, benzyl, carbethoxymethyl or carbmethoxymethyl;
$R^1$ and $R^2$ are independently, selected from hydrogen, methyl, ethyl, n-propyl, isopropyl, butyl, methoxymethyl, ethoxymethyl, methoxypropyl, aminomethyl, 2-aminoethyl, 3-aminopropyl, dimethylaminoethyl, 2-carboxyethyl, methoxycarbonylmethyl, ethoxycarbonylmethyl, pyridylmethyl, pyridylethyl, imidazolylmethyl or imidazolethyl;
X is $-CH_2O-$, $-CH_2OCH_2-$, $-CH_2O(CH_2)_2-$, $-CH_2-$ or $-CH_2CH_2-$; and
$R^3$ is 2-, or 3-pyridyl or 1- or 3-imidazolyl.

19. A method of inhibiting blood platelet aggregation of claim 18 in which the compound of said formula is selected from a group consisting of:
1,4-dihydro-2,6-di[3-pyridylmethoxy)methyl]-4-(3-nitrophenyl)pyridine-3,5-dicarboxylic acid diethyl ester,
1,4-dihydro-2,6-di[(3-pyridyloxy)methyl]-4-(3-nitrophenyl)pyridine-3,5-dicarboxylic acid diethyl ester,
1,4-dihydro-2,6-di[2-imidazol-1-yl)ethyl]-4-(3-nitrophenyl)pyridine-3,5-dicarboxylic acid diethyl ester, and
1,4-dihydro-2,6-di[(3-pyridylmethoxy)methyl]-4-(2-nitrophenyl)pyridine-3,5-dicarboxylic acid diethyl ester.

20. A method of inhibiting thromboxane synthetase in a mammal, including man, in need thereof, comprising administering to such mammal an amount effective to inhibit thromboxane synthetase of a compound of the formula

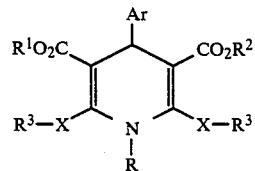

or a pharmaceutically acceptable salt thereof, wherein
Ar is 2- or 3-nitrophenyl, 2,3-dinitrophenyl, 2-3,dichlorophenyl, 3-chloro-2-nitrophenyl, 2-chloro-3-nitrophenyl, 2-trifluoromethylphenyl, pentafluorophenyl, naphthyl, pyridyl, mono-chloropyridyl, or 4- or 7-benzimidazolyl;
R is hydrogen, methyl, ethyl, n-propyl, isopropyl, benzyl, carbethoxymethyl or carbmethoxymethyl;
$R^1$ and $R^2$ are independently, selected from hydrogen, methyl, ethyl, n-propyl, isopropyl, butyl, methoxymethyl, ethoxymethyl, methoxypropyl, aminomethyl, 2-aminoethyl, 3-aminopropyl, dimethylaminoethyl, 2-carboxyethyl, methoxycarbonylmethyl, ethoxycarbonylmethyl, pyridylmethyl, pyridylethyl, imidazolylmethyl or imidazolethyl;
X is $-CH_2O-$, $-CH_2OCH_2-$, $-CH_2O(CH_2)_2-$, $-CH_2-$ or $-CH_2CH_2-$; and $R^3$ is 2-, or 3-pyridyl or 1- or 3-imidazolyl.

21. A method of inhibiting blood platelet aggregation of claim 20 in which the compound of said formula is selected from a group consisting of:
1,4-dihydro-2,6-di[3-pyridylmethoxy)methyl]-4-(3-nitrophenyl)pyridine-3,5-dicarboxylic acid diethyl ester,
1,4-dihydro-2,6-di[(3-pyridyloxy)methyl]-4-(3-nitrophenyl)pyridine-3,5-dicarboxylic acid diethyl ester,
1,4-dihydro-2,6-di[2-imidazol-1-yl)ethyl]-4-(3-nitrophenyl)pyridine-3,5-dicarboxylic acid diethyl ester, and
1,4-dihydro-2,6-di[(3-pyridylmethoxy)methyl]-4-(2-nitrophenyl)pyridine-3,5-dicarboxylic acid diethyl ester.

22. A method of inhibiting phospholipase $A_2$ ($PLA_2$) in a mammal, including man, in need thereof, comprising administering to such mammal an amount effective to inhibit phospholipase $A_2$ ($PLA_2$) of a compound of the formula

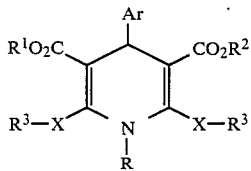

or a pharmaceutically acceptable salt thereof, wherein

Ar is 2-nitrophenyl;
$R^1$ and $R^2$ are, independently, methyl or ethyl;
X is $-CH_2OCH_2-$, $-CH_2O-$ or $-CH_2O(CH_2)_2-$; and
$R^3$ is 3-pyridyl or 1-imidazolyl.

23. A method of inhibiting phospholipase $A_2$ ($PLA_2$) of claim 22 in which the compound of the formula is 1,4-dihydro-2,6-di-[(3-pyridylmethoxy)methyl]-4-(2-nitrophenyl)pyridine-3,5-dicarboxylic acid diethyl ester.

* * * * *